United States Patent [19]

Wilson et al.

[11] Patent Number: 4,834,742
[45] Date of Patent: * May 30, 1989

[54] FASTENING SYSTEM FOR A DISPOSABLE ABSORBENT GARMENT

[75] Inventors: John C. Wilson, Neenah; Robert A. Stevens, Appleton; Thomas W. Odorzynski, Green Bay; Bruce M. Siebers, Appleton; Gregory J. Rajala, Neenah, all of Wis.

[73] Assignee: Kimberly-Clark Corporation, Neenah, Wis.

[*] Notice: The portion of the term of this patent subsequent to Oct. 20, 2004 has been disclaimed.

[21] Appl. No.: 89,660

[22] Filed: Aug. 25, 1987

Related U.S. Application Data

[63] Continuation-in-part of Ser. No. 902,828, Sep. 3, 1986, abandoned, and a continuation-in-part of Ser. No. 947,941, Dec. 31, 1986, abandoned.

[51] Int. Cl.⁴ .............................................. A61F 13/16
[52] U.S. Cl. .................... 604/389; 604/386; 604/391
[58] Field of Search ................. 24/DIG.29, DIG. 11, 24/442; 604/386, 389, 391

[56] References Cited

U.S. PATENT DOCUMENTS

| | | |
|---|---|---|
| 2,524,842 | 10/1950 | Slamon et al. ............... 24/DIG. 11 |
| 2,936,758 | 5/1960 | Csulits .................................. 604/386 |
| 3,146,778 | 9/1964 | Krawiec ...................... 24/DIG. 11 |
| 3,599,640 | 8/1971 | Larson . |
| 3,653,381 | 4/1972 | Warnken ............................. 604/391 |
| 3,882,871 | 5/1975 | Taniguchi ........................... 604/391 |
| 4,022,210 | 5/1977 | Glassman ........................... 604/359 |
| 4,036,233 | 7/1977 | Kozak . |
| 4,166,464 | 9/1979 | Korpman ........................... 604/370 |
| 4,205,679 | 6/1980 | Repke et al. ....................... 604/394 |
| 4,229,835 | 10/1980 | Shaw . |
| 4,259,957 | 4/1981 | Sonenstein et al. .................. 604/391 |
| 4,338,939 | 7/1982 | Daville . |
| 4,615,695 | 10/1986 | Cooper . |
| 4,636,207 | 1/1987 | Buell . |
| 4,642,110 | 2/1987 | Dudek . |
| 4,657,539 | 4/1987 | Hasse . |
| 4,662,877 | 5/1987 | Williams . |
| 4,701,172 | 10/1987 | Stevens ........................... 604/385.2 |

FOREIGN PATENT DOCUMENTS 155155A 9/1985 European Pat. Off. .

Primary Examiner—C. Fred Rosenbaum
Assistant Examiner—Denise Whelton
Attorney, Agent, or Firm—John Chiatalas

[57] ABSTRACT

A disposable absorbent garment (10) of the type having opposed waistband portions (14) separated by an intermediate portion (16), comprises a breathable elastomeric nonwoven fabric outer cover (12) having an absorbent structure (32) integral therewith, including a liquid-impervious baffle (36), a liquid-pervious bodyside liner (34), and an absorbent core (38) therebetween. The absorbent structure (32) preferably forms an insert attached to the outer cover (12) without restricting the stretchability thereof. The garment (10) has a generally asymmetrical hourglass profile with leg cut-out openings (18) converging together to define a narrow crotch with front (28) and rear (30) panels on either side thereof, having pairs of front (20, 22) and rear (24, 26) ear portions, respectively. Laterally-opposed pairs of rear fastener members (42, 44) and front (46, 48) fastener members extend across the rear ear portions (20, 22) and front ear portions (24, 26), respectively. Longitudinally opposed pairs (42, 46; 44, 48) of the fastener members are engagable with one another, forming substantially full-length closures from the waistband (14) to each leg opening (18) of the garment (10). Each fastener member (42, 46; 44, 48) comprises at least two spaced snap elements (50A, 50B), representing primarily fixed-point closures, separated by an abutment surface (52, 54, 56, 58) presenting a secondary load-bearing closure, such as a cohesive adhesive strip (64), for effecting and maintaining a substantially continuous closure between the primary closures formed by the snap elements (50A, 50B) when longitudinally opposed pairs (42, 46; 44, 48) of the fastener members are fastened together about the body of a wearer, providing full-length, fixed-point fastening substantially from waist to leg of the wearer, resulting in a neat, trim fit and appearance.

25 Claims, 5 Drawing Sheets

FASTENING SYSTEM FOR A DISPOSABLE ABSORBENT GARMENT

TECHNICAL FIELD

The instant invention relates to fastening systems for disposable absorbent garments, such as diapers and the like.

BACKGROUND OF THE INVENTION

Presently, disposable absorbent garments, particularly diapers, use tapes that, although manufactured to be resealable, are subject to contamination by baby powder, oil or other substances which prevent them from sealing or resealing. Accordingly, manufacturers have grappled with the problem of providing a tape which is always resealable yet has strong enough adhesive properties not to be easily unfastenable by babies. Further, the fastening tapes used on the present disposable diapers can also have a detrimental effect upon fit. Because the tapes are made to be sealable on any portion of the outer cover, and there is no indication to mothers where the tape should be sealed, the tapes are very often sealed to the outer cover at the wrong position which has several detrimental effects. First, the diaper does not fit on the baby properly, for example, if too loose, the diaper falls down or droops at the waist, or if too tight, causes strain in the outer cover which can make the baby uncomfortable; moreover, stress develops across the lower abdominal portion, causing the portion of the diaper above the stress line to fold outwardly away from the body, which exposes wet absorbent material to the outer clothing and allows the clothing to also become wet by contact therewith, often even causing the clothing, e.g., undershirts and pajama tops to become tucked into the waist of the diaper. Secondly, the improper positioning of the tapes can cause the leg openings to gap, thus causing leakage. Third, in an attempt to reposition the tapes to correct the above problems, mothers have found that there is an increased potential to contaminate the tapes, thus causing the disposable diaper to be unusable; further, repositioning of the tapes frequently tears the waterproof outer cover if the adhesive is too aggressive.

Prior designs have also centered around using a disposable or nondisposable absorbent insert in a diaper cover or baby pant, which may have waist and/or leg elastics. U.S. Pat. No. 4,425,128 to Motomura discloses a waterproof baby pant having waist elastics and leg elastics with snaps for securing an absorbent thereto. However, this diaper cover does not provide a full-length closure system from waist to leg and is not designed to be an integral disposable absorbent garment that is form-fitting or self-adjusting.

As can be seen above, current integral disposable absorbent garments, especially diapers, do not employ fixed position, full-length fastening closures; moreover, reusable baby pants do not offer the convenience and other advantages of integral disposable diapers.

SUMMARY OF INVENTION AND ADVANTAGES

According to the instant invention, there is provided a disposable absorbent garment comprising a generally rectangular outer cover having waistband portions at each longitudinal end thereof with an intermediate portion interconnecting the waistband portions and marginal portions along each lateral side edge of the outer cover. The outer cover delimits a pair of leg openings along each of the marginal portions and ear portions at each corner thereof. The ear portions extend substantially between the opposed waistband portions and each of the leg openings, respectively, with longitudinally opposed pairs of ears being engageable with one another about the body of a wearer.

An absorbent structure, including a liquid pervious body-side liner, a liquid impervious barrier means and an absorbent core disposed therebetween, is superposable on the outer cover and associated therewith.

A fixed-position, full-length fastening system comprises a plurality of fastener members each fixedly attached to one of the ear portions and extending thereacross substantially from an associated waistband portion to the marginal leg opening, with longitudinally opposed ones of the fastener members being engageable with one another about the body of a wearer.

Each fastener member includes at least two snap elements spaced from one another in essentially coplanar relationship and engageable with a cooperating pair of snap elements similarly situated on a longitudinally opposed fastener member, forming a primary load bearing closure. The pairs of spaced snap elements on each fastener member are separated by an abutment surface presenting cooperable secondary load bearing closure means for effecting and maintaining a substantially continuous closure between the primary snap closure when longitudinally opposed pairs of the fastener members are fastened together, providing full-length, fixed point fastening substantially from waist to leg of a wearer.

An advantage of the instant invention is the provision of a fixed point full-length fastener member that combines the beneficial attributes of various fastener elements in a unitary construction, providing a continuous closure from waist to leg of the garment for improved fit and containment.

A further advantage of the instant invention is the ease of fastening and refastening the closure system for a predetermined fit.

DETAILED DESCRIPTION OF THE PREFERRED EMBODIMENTS

Figure 1:
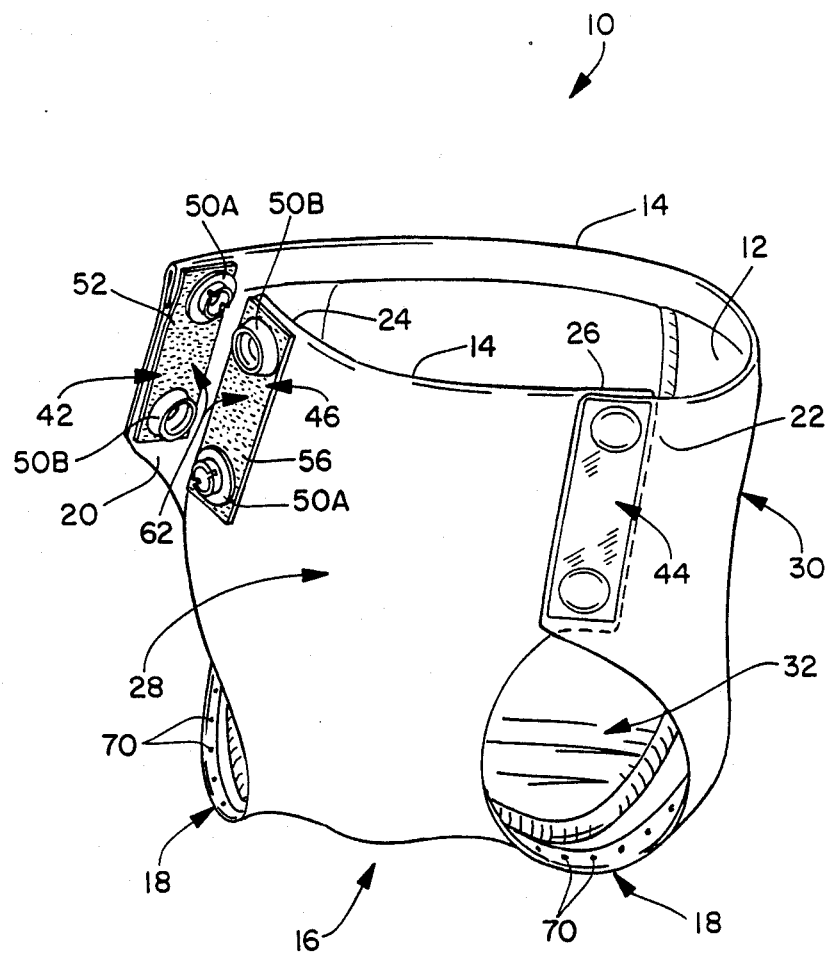
FIG. 1 is a perspective view of the invention.
Figure 2:
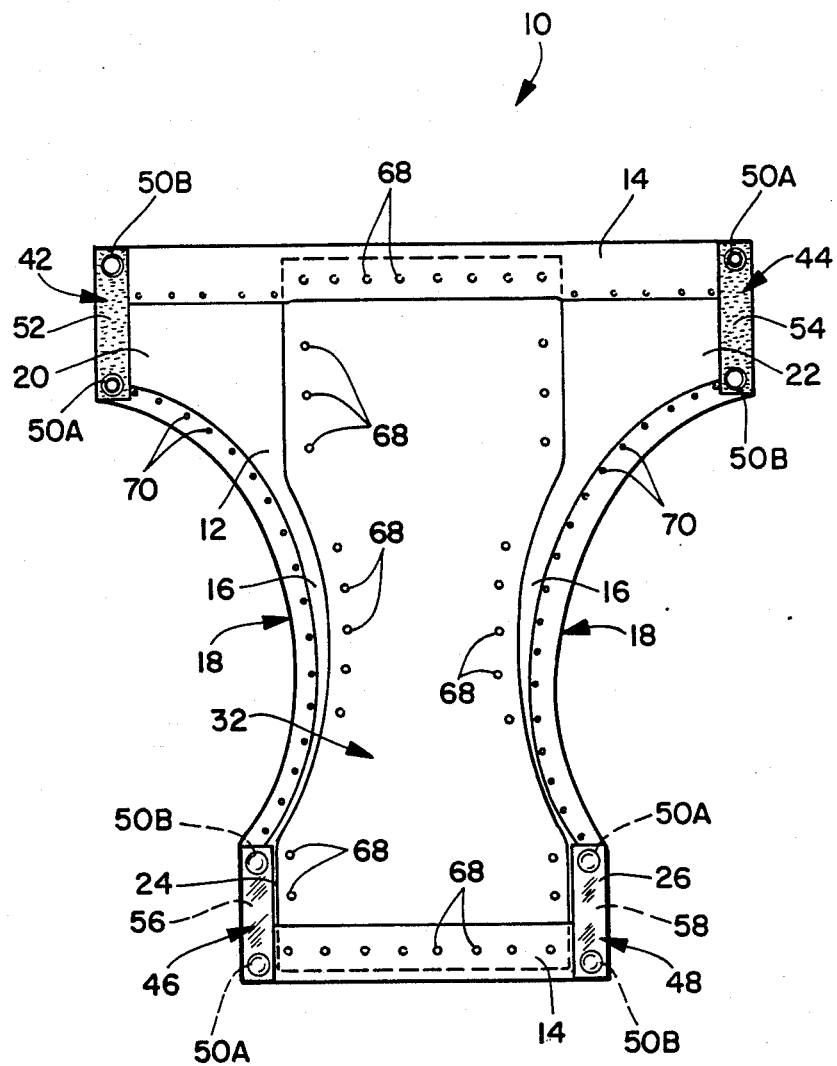
FIG. 2 is a plan view of the invention, showing the bodyside of the instant garment.

Referring to FIGS. 1 and 2, according to the instant invention, there is provided a disposable absorbent garment, generally shown at 10, such as a disposable diaper, feminine napkin or incontinent garment, comprising a generally rectangular backsheet or outer cover, generally indicated at 12, having waist band portions 14 at each longitudinal end thereof with an intermediate portion, generally shown at 16, interconnecting the waistband portions 14. A pair of leg openings, generally indicated as 18, are delimited along marginal portions of each lateral side edge of the outer cover 12. Ear portions 20, 22, 24, 26 are delimited at each corner of the outer cover 12 and extend substantially between the opposed waistband portions 14 and each of the marginal leg openings 18, respectively, with longitudinally opposed pairs of ears 20, 24 and 22, 26 being engageable with one another about the body of a wearer, such as a baby. The outer cover 12 preferably comprises an airpervious elastomeric nonwoven fabric, resiliently stretchable more than about 20 percent but preferably in the range of 20 to 200 percent in at least one direction. Preferably the outer cover 12 further comprises an asymmetrical hourglass profile with the leg openings 18 cut out from the intermediate portion 16 thereof, defining a front panel 28 having a laterally opposed pair of front ear portions 24, 26 in conjunction therewith and a rear panel 30, larger in area than the front panel 28 and having another laterally opposed pair of rear ear portions 20, 22 in conjunction therewith. The front 28 and rear 30 panels are separated from one another by a narrowed crotch portion formed from the intermediate portion 16 by the converging leg cut-out openings 18.

Figure 3:
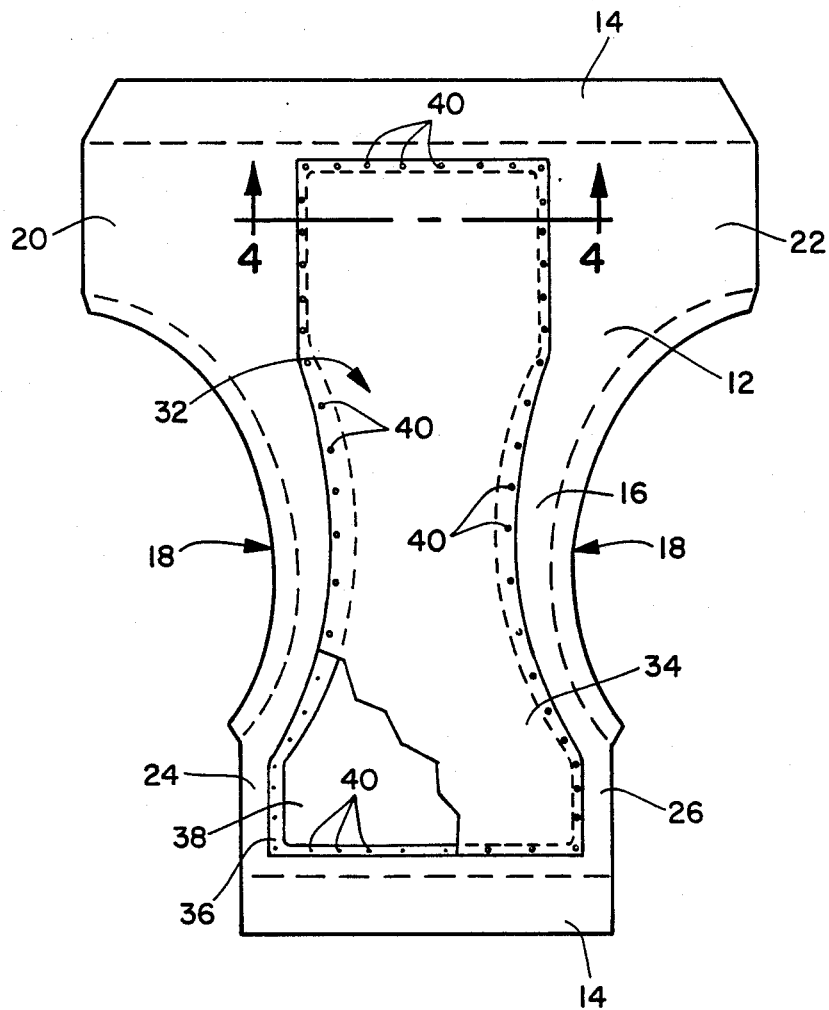
FIG. 3 is a plan view of the invention, partially cut away to show the absorbent structure and otherwise showing the garment of the present invention in a semi-finished condition.
Figure 4:
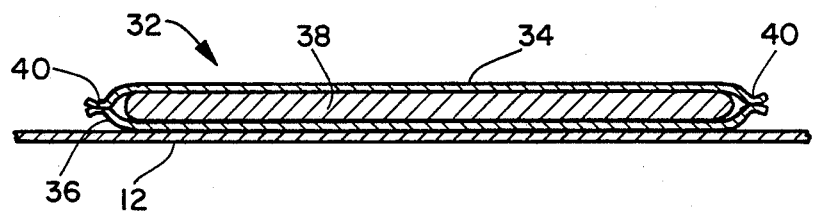
FIG. 4 is a sectional view of cross-section 4—4 of FIG. 3.
Figure 5:
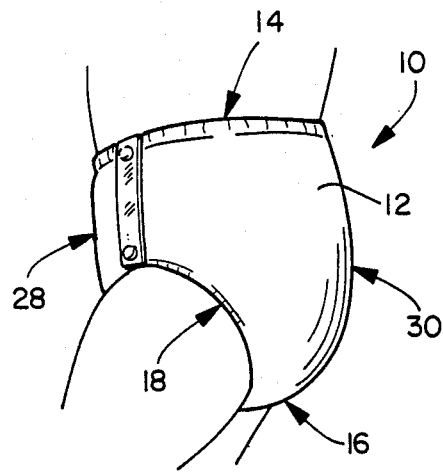
FIG. 5 is a side view of the disposable absorbent garment of the present invention shown secured around a baby.
Figure 6:
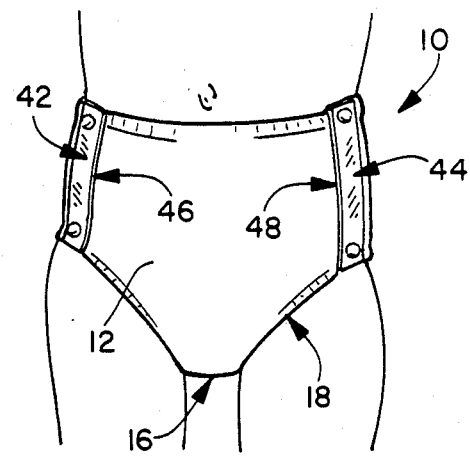
FIG. 6 is a front view of the disposable absorbent garment of the present invention shown secured around a baby.
Figure 7:
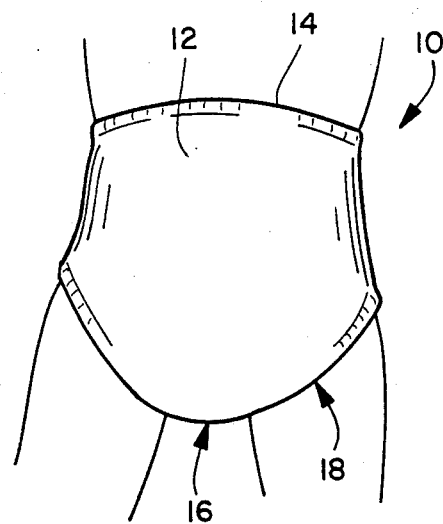
FIG. 7 is a back view of the disposable absorbent garment of the present invention shown secured around a bay.

With reference to FIGS. 2, 3 and 4, an absorbent structure, generally indicated at 32, superposable on the backsheet 12 and integral therewith, includes a liquid-pervious bodyside liner means, for example, a spun-bonded polypropylene of the type presently available commercially, a liquid-impervious baffle means 36, for example, a plastic film of polyethylene, polypropylene or the like, such as is commercially available, and an absorbent core 38 disposed between the liquid-pervious liner 34 and liquid-impervious baffle means 36. Where the outer cover 12 is a conventional plastic film of the type not resiliently stretchable, the separate liquid-impervious baffle 36 is not required so that the absorbent core 38 is sandwiched between the bodyside liner 34 and the outer cover 12, which are secured together. Preferably, however, the absorbent structure 32 is in the form of a separate, independent insert, including the bodyside liner 34, liquid-impervious barrier 36 and absorbent core 38 sandwiched therebetween. The absorbent structure 32 shown is substantially nonstretchable and fully integrated into the stretchable outer cover 12 without restricting the stretchability thereof. As shown in FIGS. 3 and 4, ultrasonic or thermal bonds 40 secure the absorbent structure 32 together by bonding the liner 34 and barrier 36 to one another around their common peripheral edges with the absorbent core 38 therebetween.

Referring to FIGS. 1 and 2, the invention further comprises a fixed-position, full-length fastening system wherein a plurality of fastener members 42, 44, 46 and 48 are fixedly attached to the ear portions 20, 22, 24 and 26, respectively, extending across the pairs of front 20, 22 and rear 24, 26 ear portions substantially from an associated waistband portion 14 to the marginal leg openings 18. Longitudinally-opposed pairs 42, 46 and 44, 48 of said fastener members are engageable with one another about the body of a wearer. The invention includes primary load-bearing garment closure wherein the pair of laterally opposed rear fastener members 42, 44, each preferably include male 50A and female 50B snap elements, spaced from one another in essentially coplanar relationship and releasably engageable with cooperating spaced female 50B and male 50A snap elements similarly situated on said pair of longitudinally opposed front fastener members 46, 48. The alternating spaced male 50A and female 50B snap pattern shown in FIGS. 1 and 2 may instead comprise cooperating pairs of spaced male or female snaps, so that longitudinally opposed pairs of fastener members 42, 46; 44, 48 have mating sets of snap elements. Each pair of snap elements 50A, 50B on said fastener members 42, 44, 46, 48 are separated by abutment surfaces 52, 54, 56, 58, respectively, presenting secondary load-bearing closure means 60 as variously shown in FIGS. 9–11.

Figure 9:
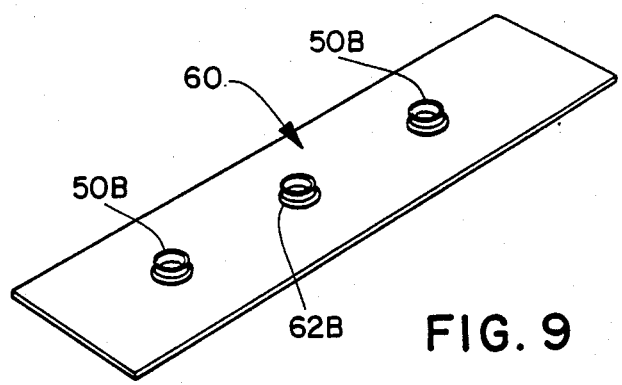
FIG. 9 is a perspective view showing an individual fastener member of the present invention.
Figure 10:
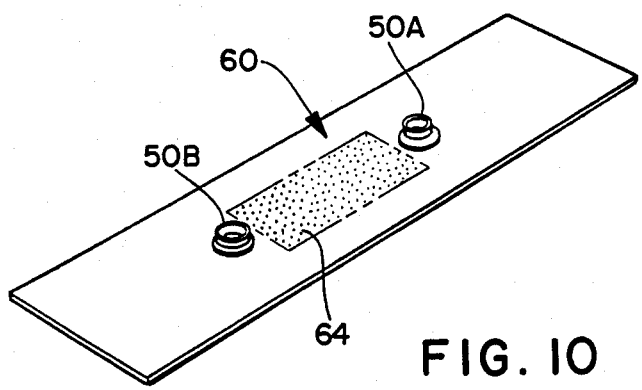
FIG. 10 is a perspective view showing another of the individual fastener members of the present invention.
Figure 11:
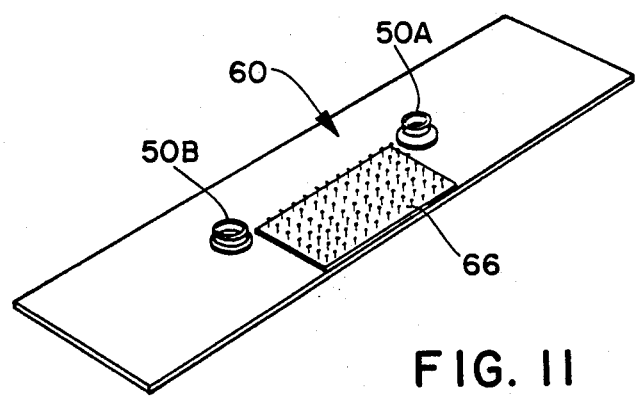
FIG. 11 is a perspective view showing a further one of the individual fastener members of the present invention.

The secondary load-bearing closure means 60 effect and maintain a substantially continuous closure between said primary snap closures when longitudinally opposed pairs 42, 46 and 44, 48 of said fastener members are fastened together, providing full-length, fixed-point fastening of the garment substantially from waist to leg of the baby. With reference to FIG. 9, the secondary load-bearing closure means 60 may take the form of a third snap set of which only a female snap 62B is shown. A cohesive material 64, as shown in FIG. 10, may preferably be provided by treating a substrate material with an adhesive having greater affinity for itself than for other materials; satisfactory adhesive materials for this purpose are NIP-WELD ™ Nos. 2082-939 and 2132-939, manufactured by Findlay Adhesive Corporation, Milwaukee, WI. A hook and loop type of material, where the hook portion 66 is shown in FIG. 11, may form the secondary closure wherein the hook and loop portions of a tape material such as Velcro ® are respectively secured on longitudinally opposed fastener member 42, 46 and 44, 48, preferably with the softer loop portion on the surface of the ear facing the skin, in case of incidental skin contact. The fastener members may be constructed from a two-ounce spunbond substrate sheet cut into generally rectangular-shaped strips having the primary snap closures 50A, 50B and the alternative secondary snap closure 62A, 62B of FIG. 9 staked onto the strip by conventional means. The snap elements 50A, 50B may be of a metal or plastic material, for example, polyacetal or polypropylene; further, as mentioned above, the pair of snap elements on longitudinally opposed fastener members may be alternating spaced male 50A and/or female 50B snap elements so that corresponding snap elements on the opposed fastener members form mating sets when engaged. A unique feature of the subject invention is that the snap pattern on the laterally 42, 44; 46, 48, as well as longitudinally (42, 46; 44, 48) opposed fastener members can be arranged to correspond (FIG. 2); as a result, disposal of the soiled garment upon removal from the body is easily accomplished, e.g., by folding and rolling the front panel 28 inwardly and then fastening the rear pair of fastener members 42, 44 to one another, thus neatly bundling the garment into a closed compact package for disposal.

With reference to FIG. 2, the laterally opposed rear fastener members 42, 44 are fixedly attached across the bodyside of the rear pair of ears 20, 22, while the other pair of laterally opposed fastener members 46, 48 are fixedly attached across the external side of the front pair of ears 24, 26, for overlying engagement of the rear pair of fastener members 42, 44 with the front pair of fastener members 46, 48. Conversely, the front pair fastener members 46, 48 may be fixedly attached across the bodyside of the front pair of ears 24, 26 and the rear pair of fastener members 42, 44 fixedly attached across the external side of the rear pair of ears, for overlying engagement of the front pair of fastener members 46, 48 with the rear pair of fastener members 42, 44, depending upon the particular fastening pattern desired.

With respect to the physical properties required of the fastening system, it has been found that the primary snap closure should have a peel strength of from about 600 grams to about 2,500 grams. Snaps having different opening strengths were evaluated in diaper wear studies wherein the minimum snap strength remaining fastened during an overnight wear period was greater than 600 grams, while the maximum snap strength at which it was difficult to either manually engage or disengage the snap elements was found to be approximately 2,500 grams. The maximum peel strength allowable for the snap closure is further dependent on the material to which the snap is staked and the ability or strength of the user, such as a parent, to open the snap. Snap strengths were quantitatively determined by a 180° peel test performed at 4.0 inches per minute. The minimal strength requirement for the secondary closure means is essentially solely dependent upon shear strength and not peel strength provided that torsional strain on the fastener member is minimized. Hook and loop materials of varying peel and shear strengths were tested, and a direct correlation found between shear strength and functionality. The minimum shear strength allowing for successful overnight wearing of the diaper was greater than about 3,750 grams per square inch. The maximum shear strength of the secondary closure is itself not critical, rather it is dependent upon the maximum shear strength for the primary snap closure. Materials were tested by a shear test wherein a sample size of bonded area, e.g. cohesive adhesive or Velcro ®, of one square inch was pulled at 4.0 inches per minute. With respect to the dimensions of the particular elements of the fastener member, it has been found that the diameter of the snap element preferably should not exceed 0.4 inches and that the ratio of the snap diameter to the minimum distance separating the snaps is preferably less than 6, expressed mathematically:

$$D/d < 6$$

where
$D$ = maximum diameter of snap
and
$d$ = minimum distance separating the respective rims of the snaps Further, it has been found that the thickness or outwardly projecting height of the snap elements 50A and 50B is preferably from about 0.01 to about 0.19 inches in order to minimize impingement upon the skin.

The instant fastening system preferably combines a hybrid of elements in cooperation with unique materials, while prior attempts to employ a single material fastening system meeting the criteria of the instant invention have been unsuccessful. The instant invention meets the criteria of a fastening system; maintaining a substantially full-length attachment from waist to leg for diapers or like garments, allowing the diaper to maintain a neat, trim garment-like appearance during wear without sagging of the waist or gapping and blousing at the hips; providing a point-to-point fastening system easy to fasten and unfasten and refastenable at least five times; and providing a system that is safe to the wearer without sharp edges or materials which would irritate the wearer. Another criterion for performance of the instant fastening system is that during wear, the waist and leg areas of the fastener experience high shear and peel forces which the instant system can withstand while maintaining a sufficient rigidity to prevent the diaper from collapsing, that is, maintaining its dimensional length. The fastening system comprises a strong durable fastening point at the waist and leg portions of the fastener and a weaker attachment site between the two strong points.

FIGS. 5-8 show a disposable diaper 10 of the instant invention as it would be worn by a baby wherein the disposable diaper has a neat, trim fit and appearance when viewed from different perspectives.

Figure 8:
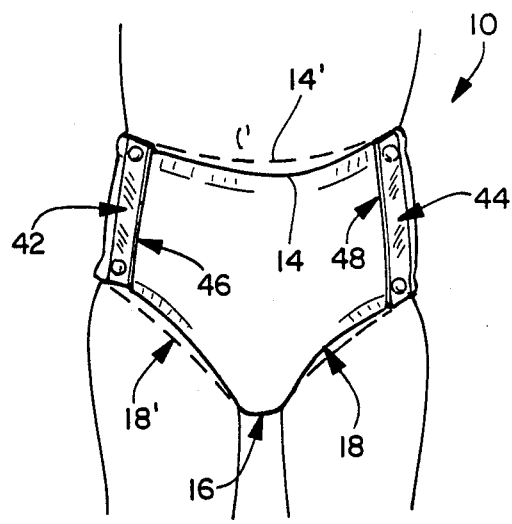
FIG. 8 is a front view of the disposable absorbent garment of the present invention showing the disposition of the garment on the baby after being worn for a period of time.

FIG. 8 illustrates the minimal extent the diaper moves or sags from an initial position as indicated by the dashed lines 18' and 14' after being worn by an infant for a period of time.

Although the stronger primary closures at the end points of each fastener member may be garment snaps, for example, a multi-component polyacetal snap, smaller snaps have been shown to be as effective; however, it is believed a large enough snap is required for easy fastening by the user. The specific snap elements shown are not the only embodiments that will produce the desired strong closure at leg and waist. There are several snap-like closures which could be equivalent, for example, the male portion of the snap could be a single stud which is snapped through an aperture in a piece of film or nonwoven, functioning as the female portion of the snap set and having a slightly smaller diameter hole than the diameter of the stud, producing an economical snap. Further, the fastener members need not be previously mounted on a separate strip as shown then bonded to the stretchable outer cover, for example, ultrasonically, as in the instant invention. Multi-component snaps are available which are bondable to a stretchable outer cover material of the type contemplated by the instant invention. An advantage of the instant system is that, due to the consumer's vast experience with snaps on infant clothing, the fastener members are easily fastened; further, the automatic fastening of the secondary closure means is effected when the two primary snap closures are made. The quantitative physical properties described above combine to define a fastening system quantitatively independent of the materials or type of mechanical fasteners employed; moreover, the resultant full-length, fixed-point fastening system produces a desirable fit and appearance.

A selection criterion for the selection of a material and design for fastener members 42, 44, 46, 48 is to consider the Moment of Inertia (I) of the material in conjunction with the Modulus of Elasticity (E). This selection criterion which involves the product of (E)(I) is utilized as follows. The value (E)(I) is determined in a material/design combination, that is, the value (E)(I)

is determined for a particular design utilizing a particular material. The value (E)(I) is calculated from the following formula taken from the textbook "Mechanical Engineering Design," 2nd Ed. by Joseph E. Shigley, Published by McGraw-Hill, 1972, page 699.

$$EI = L^3M/48$$

wherein M is the slope of the tangent to the initial straight-line portion of the load-deflection curve of deflection as obtained from ASTM test D-790 and wherein L is the support span as defined by ASTM test D-790.

In order to avoid the problem of red marking of skin, as when a baby sits down, and the fastener refuses to conform with the curves and folds of the body, it has been found that the fastener must have at least one area with a Modulus of Elasticity or stiffness of less than 0.1 pound-inches$^2$ and areas of such stiffness greater than 0.1 pound-inches$^2$ must have such areas separated by an area with stiffness less than 0.1 pound-inches$^2$ and that the area with stiffness greater than 0.1 pound-inches$^2$ and that the area greater than 0.4 inches in length, i.e., the diameter of the snap should not exceed 0.4 inches. The ratio of length (area, stiffness greater than 0.1) to the length (area, stiffness less than 0.1) should not exceed 6. Although the above criteria have been applied to the instant invention, the relationships apply equally as well to other forms of fastening systems such as zippers, buttons, clasps, etc., so that when these criteria are met, the fastener will be flexible enough to conform to the folds and creases in the body of a sitting, kneeling or crawling infant when the fastener is positioned on the diaper in the area shown in FIGS. 1, 2, 5 and 8.

The garment 10 is constructed and assembled as shown in FIGS. 2 and 3 wherein the waist areas 14 of the outer cover 12 are folded as indicated by the dotted line shown in FIG. 3 to form a hem entrapping the generally hourglass-shaped absorbent structure insert 32, which is superposable on the outer cover 12, at the longitudinal ends thereof. Ultrasonic, thermal or other autogeneous bonds 68 secure the folded over portions of the waist hems to the outer cover 12 and to the absorbent structure 32 to further attach the absorbent structure to the outer cover in the front 28 and rear 30 panels and in the crotch area of the intermediate portion 16 so that the material of the outer cover 12 may stretch around the discrete bond points, unlike seams used in conventional garments for securing operative components to one another.

The leg openings 18 are formed by cutting out converging arcuate areas from the generally rectangular outer cover 12 defining a narrowed crotch portion. The leg openings 18 are hemmed by an apparatus and method disclosed in U.S. Pat. No. 4,650,532 in the name of Kloehn, et al., and assigned to the assignee of the subject application, wherein a mandrel having an inflatable torroidal-shaped bladder attached to an end thereof, projects upwardly from the bottom or external side of the leg cut-out opening 18 and folds the leg openings 18 upwardly along the arcuate dotted lines shown in FIG. 3, then the bladder expands to fold the arcuate flap downwardly into engagement with the bodyside surface of the leg opening, forming a curved hem, as shown in FIG. 2 about the leg opening. The curved leg hem is thence secured by autogeneous and-/or adhesive bonds 70 as shown in FIG. 2. The formation of the curved hem is particularly accommodated by the stretchable material of the outer cover 12. Since the outer cover material is resiliently stretchable, the hems at the leg openings 18 and waistband portions 14 are themselves elastic and have increased tension due to the increased thickness of the material of the outer cover at the folded over hem; however, additional elastic material (not shown) can be entrapped within the waist and-/or leg hems to provide additional elastic tension. Further, the peripheral edges of the absorbent insert may be elasticized, causing the longitudinal ends of the absorbent structure to converge, forming a cupped shape. Material suitable for such additional elastication of the leg and waistband portions is FULLASTIC, a material sold by H. B. Fuller Company of Minneapolis, Minn.

The outer cover 20 of the present invention is preferably made from a resiliently stretchable material having a stretchability of from about 20 percent to about 200 percent. The term stretchability as used herein is defined by the following relationship:

stretchability = ((final dimension - initial dimension)/initial dimension) × 100%

Since the outer cover 20 is also resilient, the outer cover returns essentially to its initial dimension when the stretching force is removed.

One such resiliently stretchable material is disclosed in U.S. Pat. No. 4,663,220 in the name of Tony J. Wisneski and Michael T. Morman, assigned to the assignee of the present application, entitled "Polyolefin-containing Extrudable Compositions and Methods for their Formation Into Elastomeric Products", the disclosure of which is incorporated herein by reference and relied upon. That application provides extrudable elastomeric compositions which, after extrusion, solidify to form elastomeric products such as, for example, fibrous nonwoven elastomeric webs. As used herein and in the referenced U.S. Pat. No. 4,663,220, the term 'nonwoven web' means a web of material which has been formed without use of weaving processes which produce a structure of individual fibers or threads which are interwoven in an identifiable repeating manner. Nonwoven webs have been, in the past, formed by a variety of processes such as, for example, meltblowing processes, spunbonding processes, film aperturing processes and staple fiber carding processes. The extrudable elastomeric compositions are blends of (1) from at least about 10 percent, by weight, of an A-B-A' block copolymer, where "A" and "A'" are each a thermoplastic polymer endblock which includes a styrenic moiety such as a poly(vinyl arene) and where "B" is an elastomeric poly-(ethylene-butylene) midblock, with (2) from greater than 0 percent, by weight, to about 90 percent, by weight, of a polyolefin which, when blended with the A-B-A' block copolymer and subjected to appropriate elevated pressure and elevated temperature conditions, is extrudable, in blended form, with the A-B-A' block copolymer. The A-B-A' block copolymer serves to impart elastomeric properties to products formed from the extrudable composition and the presence of the polyolefin in the blend serves to reduce the viscosity of the composition as compared to the viscosity of the neat, that is, pure, A-B-A' block copolymer and thus enhances the extrudability of the composition.

Preferably, the "A" and "A'" thermoplastic styrenic moiety containing endblocks of the block copolymer are selected from the group including polystyrene and polystyrene homologs such as, for example, poly(alpha-methylstyrene). In some embodiments the "A" and "A'" thermoplastic styrenic moiety containing endblocks are identical. Preferably, the polyolefin is selected from the group including at least one polymer selected from the group including polyethylene, polypropylene, polybutene, ethylene copolymers, propylene copolymers, butene copolymers or blends of two or more of these materials.

The blend usually includes from at least about 20 percent, by weight, to about 95 percent, by weight, of the block copolymer and from at least about 5 percent, by weight, to about 80 percent, by weight, of the polyolefin. For example, the blend may include from about 30 percent, by weight, to about 90 percent, by weight, of the block copolymer and from about 10 percent, by weight, to about 70 percent, by weight, of the polyolefin. Preferably, the blend includes from about 50 percent, by weight, to about 90 percent, by weight, of the block copolymer and from about 10 percent, by weight, to about 50 percent, by weight, of the polyolefin. For example, the blend may include from about 50 percent, by weight, to about 70 percent, by weight, of the block copolymer and from about 30 percent, by weight, to about 50 percent, by weight, of the polyolefin. One blend includes about 60 percent, by weight, of the polyolefin.

The extrudable composition is extruded or otherwise formed, such as, for example, by molding, for example, injection molding, at an appropriate, that is effective, combination of elevated pressure and elevated temperature conditions. These conditions will vary depending on the polyolefin utilized. For example, the extrudable composition should be extruded or otherwise formed at a temperature of at least about 125 degrees Centigrade if polyethylene is utilized as the polyolefin in the blend or at least about 175 degrees Centigrade if polypropylene is utilized in the blend, for example, at a temperature of from at least about 290 degrees Centigrade to about 345 degrees Centigrade, more specifically, at a temperature of from at least about 300 degrees Centigrade to about 335 degrees Centigrade, into elastomeric products such as, for example, elastomeric fibers, which may be collected as a fibrous nonwoven elastomeric web.

Preferably the blends are extrudable within the above-defined temperature ranges at elevated pressures within the die tip, (for example, within the extrusion capillaries of a die tip having thirty (30) extrusion capillaries per lineal inch of die tip with each of the capillaries having a diameter of 0.0145 inches and a length of 0.113 inches) of no more than about 300 pounds per square inch, gage, for example, from pressures of from about 20 pounds per square inch, gage, to about 250 pounds per square inch, gage. More specifically, the blends are extrudable within the above-defined temperature ranges at pressures of from about 50 pounds per square inch, gage, to about 250 pounds per square inch, gage, for example, from about 125 pounds per square inch, gage, to about 225 pounds per square inch, gage. Higher elevated pressures can be utilized with other die designs having a lower number of capillaries per inch of die, but, generally speaking, lower production rates result.

Importantly, it has been found that the extrudable compositions are extrudable at satisfactory throughput rates because the presence of the polyolefin in the extrudable composition reduces the viscosity of the extrudable composition, as compared to the viscosity of the neat, that is, pure, block copolymer, to satisfactory levels. This reduced viscosity proportionally reduces the die tip pressure if all other parameters remain the same. For example, the viscosity of the extrudable compositions will generally be less than about 500 poise when extruded at the above-defined elevated temperature and elevated pressure ranges. Preferably, the viscosity of the extrudable composition is less than about 300 poise when extruded at the above-defined elevated temperatures and elevated pressure ranges. For example, the viscosity of the extrudable composition may be from at least about 100 poise to about 200 poise when extruded at the above-identified elevated temperature and elevated pressure conditions.

Because the polyolefin reduces the viscosity of the blend, as compared to the viscosity of the block copolymer, the extrudable composition is extrudable within the above-identified elevated temperature and elevated pressure ranges, through a die tip having, for example, thirty capillaries per inch of die tip with the capillaries having a diameter of about 0.0145 inches and a length of about 0.113 inches at a rate of from at least about 0.02 grams per capillary per minute to about 1.7 or more grams per capillary per minute. For example, the extrudable composition may be extruded through the above-identified die tip having capillaries with a diameter of about 0.0145 inches and a length of about 0.113 inches at the rate of from at least about 0.1 grams per capillary per minute to about 1.25 grams per capillary per minute. Preferably, the extrudable composition is extrudable through the above-identified die tip having capillaries with a diameter of about 0.0145 inches and a length of about 0.113 inches at the rate of from at least about 0.3 grams per capillary per minute to about 1.1 grams per capillary per minute.

The extrudable composition may be formed into fibrous nonwoven elastomeric webs preferably having microfibers with an average diameter of not greater than about 100 microns, and preferably having an average basis weight of not more than about 300 grams per square meter, for example, an average basis weight of from about 5 grams per square meter to about 100 grams or more per square meter. More specifically, an average basis weight of from about 10 grams per square meter to about 75 grams per square meter. For example, a fibrous nonwoven elastomeric web may be formed by extruding the extrudable composition at an appropriate, that is, effective, combination of elevated temperature and elevated pressure conditions. Preferably, the extrudable composition is extruded at a temperature of from at least about 125 degrees Centigrade if the polyolefin is polyethylene or at least about 175 degrees Centigrade if the polyolefin is polypropylene, for example, from about 290 degrees Centigrade to about 345 degrees Centigrade, more specifically from about 300 degrees Centigrade to about 335 degrees Centigrade. Preferably, the extrudable composition is extruded within the above-identified temperature ranges and pressures, within the die tip, (for example, within the extrusion capillaries of a die tip having thirty (30) extrusion capillaries per lineal inch of die tip with each of the capillaries having a diameter of about 0.0145 inches and a length of 0.113 inches) of no more than about 300 pounds per square inch, gage, for example, from about 20 pounds per square inch, gage, to about 250 pounds per square inch, gage. More specifically, the extrudable composition is extruded at a pressure within the capillaries of the above-identified die tip of from about 50 pounds per square inch, gage, to about 250 pounds per square inch, gage, for example, from about 125 pounds per square inch, gage, to about 225 pounds per square inch, gage.

In the formation of elastomeric nonwoven webs, the extrudable composition is extruded, at the above-defined elevated temperature and elevated pressure conditions at a rate of from at least about 0.02 gram per capillary per minute to about 1.7 or more grams per capillary per minute, for example, from at least about 0.1 gram per capillary per minute to about 1.25 grams per capillary per minute, more specifically, from at least about 0.3 gram per capillary per minute to about 1.1 grams per capillary per minute, through a die having a plurality of small diameter extrusion capillaries, as molten threads into a gas stream which attenuates the molten threads to provide a gas-borne stream of microfibers which are then formed into the fibrous nonwoven elastomeric web upon their deposition on a collecting arrangement. The attenuating gas stream is applied to the molten threads at a temperature of from at least about 100 degrees Centigrade to about 400 degrees Centigrade, for example, from about 200 degrees Centigrade to about 350 degrees Centigrade and at a pressure of from at least about 0.5 pound per square inch, gage, to about 20 pounds per square inch, gage, for example, from at least about 1 pound per square inch, gage, to about 10 pounds per square inch, gage. The thread attenuating gas stream may be an inert, non-oxidizing, gas stream such as, for example, a stream of nitrogen gas. In some embodiments the velocity and temperature of the thread-attenuating gas stream is adjusted so that the fibers are collected as substantially continuous fibers having diameters of from about ten (10) microns to about sixty (60) microns, for example, from at least about ten (10) microns to about forty (40) microns. The fibrous nonwoven elastomeric webs so formed will include elastomeric fibers composed of from at least about 10 percent, by weight, of the block copolymer and greater than 0 percent, by weight, and up to about 90 percent, by weight, of the polyolefin. The fibers are usually composed from at least about 20 percent, by weight, to about 95 percent, by weight, of the block copolymer and from at least about 5 percent, by weight, to about 80 percent, by weight of the polyolefin. For example, the fibers may be composed from at least about 30 percent, by weight, to about 90 percent, by weight, of the block copolymer and from at least about 10 percent, by weight, to about 70 percent, by weight, of the polyolefin. Preferably, the fibers are composed from about 50 percent, by weight, to about 90 percent, by weight, of the block copolymer and from at least about 10 percent, by weight, to about 50 percent, by weight, of the polyolefin. For example, the fibers may be composed from at least about 50 percent, by weight, to about 70 percent, by weight, of the block copolymer and from at least about 30 percent, by weight, to about 50 percent, by weight, of the polyolefin.

Another such resiliently stretchable material is disclosed in U.S. Patent Application, Ser. No. 760,437 in the name of Jack D. Taylor and Michael J. Vander Wielen and assigned to the assignee of the present application, entitled "Composite Elastomeric Material and Process for Making the Same", the disclosure of which is incorporated herein by reference and relied upon. That application provides a method of producing a composite elastic material comprising at least one gatherable web bonded to at least one elastic web, the method comprising (a) tensioning an elastic web (which may comprise a fibrous web such as a nonwoven web of elastomeric fibers, for example, meltblown elastomeric fibers) to elongate it; (b) bonding the elongated elastic web to at least one gatherable web under conditions which soften at least portions of the elastic web to form a bonded composite web; and (c) relaxing the composite web immediately after the bonding step whereby the gatherable web is gathered to form the composite elastic material. The fibrous elastic web can also be maintained in a stretched condition during the bonding, at an elongation of at least about 25 percent, preferably about 25 percent to over 500 percent, for example, about 25 percent to 550 percent elongation during the bonding. The method also includes bonding the elongated elastic web to the gatherable web by overlaying the elastic and gatherable webs and applying heat and pressure to the overlaid webs, for example, by heating bonding sites on the elastic web to a temperature of from at least about 65 degrees Centigrade to about 120 degrees Centigrade, preferably from at least about 70 degrees Centigrade to about 90 degrees Centigrade.

That application also provides an elastic composite material comprising an elastic web bonded to at least one. gatherable web which is extensible and contractible with the elastic web upon stretching and relaxing of the composite material, the elastic composite material being made by a method as described above. Also provided is an elastic web that is bonded to the gatherable web at a plurality of spaced-apart locations in a repeating pattern and the gatherable web is gathered between the bonded locations. The elastic web may comprise a nonwoven web of elastomeric fibers, preferably elastomeric microfibers, such as, for example, an elastomeric nonwoven web of meltblown elastomeric fibers or an elastomeric film.

The elastic composite material may include one or more of the following in any combination: the elastomeric fibers, preferably meltblown elastomeric fibers, may be formed from material selected from the group including (i) A-B-A' block copolymers wherein "A" and "A'" may be the same or different endblocks and each is a thermoplastic polymer endblock or segment which contains a styrenic moiety such as polystyrene or polystyrene homologs, and "B" is an elastomeric polymer midblock or segment, for example, a midblock selected from the group including poly(ethylene-butylene), polyisoprene and polybutadiene, with poly(ethylene-butylene) being preferred and (ii) blends of one or more polyolefins with the A-B-A' block copolymers of (i) where "B" is a poly(ethylene-butylene) midblock; each of the "A" and "A'" endblocks may be selected from the group consisting of polystyrene and polystyrene homologs, for example, poly(alpha methylstyrene), and where the elastomeric fibers are formed from a blend of one or more polyolefins with an A-B-A' block copolymer where "B" is a poly(ethylene-butylene) midblock, the polyolefin is selected from one or more of polyethylene, polypropylene, polybutene, ethylene copolymers, propylene copolymers and butene copolymers; the elastomeric film and the elastomeric fibers which form the elastomeric nonwoven web, for example, the meltblown microfibers, are composed of at least 10 percent, for example at least 20 percent, more specifically at least 30 percent, for example, from about 10 percent to 90 percent, by weight, of the aforesaid A-B-A' block copolymers and greater than 0 percent, by weight, for example, from about 90 percent to about 10 percent, by weight, of the polyolefin; the elastic web, for example, a fibrous elastic web, is bonded to the gatherable web at a plurality of spaced-apart locations in a repeating pattern and the gatherable web is gathered between the bonded locations; the elastic web preferably has a low basis weight of from about 5 to about 300, preferably from about 5 to about 200, grams per square meter, for example, from about 5 to about 100 grams per square meter, although its basis weight can be much higher; the gatherable web is a nonwoven, non-elastic material, preferably one composed of fibers formed from materials selected from the group including polyester fibers, for example, poly(ethylene terephthalate) fibers, polyolefin fibers, polyamide fibers, for example, nylon fibers, cellulosic fibers, for example, cotton fibers, and mixtures thereof. Alternatively, the gatherable web may be any suitable woven fabric. In a particular aspect, the composition of the A-B-A' polymer used is such that the sum of the molecular weight of "A" with the molecular weight of "A'" is from about 14 to 31 percent (from about 14 to 29 percent when "B" is poly(ethylene-butylene)) of the molecular weight of the A-B-A' block copolymer.

A further such resiliently stretchable material is disclosed in U.S. Pat. No. 4,657,802, in the name of Michael J. Morman, and assigned to the assignee of the present invention, entitled "Composite Nonwoven Elastic Web", the disclosure of which is incorporated herein by reference. That application is directed to a process for producing a composite nonwoven elastic web which is composed of a nonwoven elastic web that is joined to a fibrous nonwoven gathered web. In particular, the process disclosed therein produces a composite nonwoven elastic web which, in its relaxed, nonstretched state, is composed of a gathered nonwoven fibrous web that is joined to a nonwoven elastic web with the nonwoven elastic web having been relaxed from a stretched, biased length to a relaxed, unbiased, nonstretched length so as to gather the fibrous nonwoven gathered web. An important feature of the process disclosed therein is that the fibrous nonwoven gatherable web is formed directly onto a surface of the nonwoven elastic web while the nonwoven elastic web is maintained in a stretched, biased and elongated condition. The nonwoven elastic web may be formed by, for example, a meltblowing process or any other process for forming a nonwoven elastic web. For example, the nonwoven elastic web could be an apertured web of an elastic film as opposed to a meltblown fibrous nonwoven elastic web. The formed nonwoven elastic web has a normal relaxed, nonstretched, nonbiased length. Thereafter, the nonwoven elastic web is elongated by being stretched to a stretched, biased length. In a subsequent step of the process a fibrous nonwoven gatherable web may be formed, for example, by either a meltblowing or spinbonding process or any other process for forming a fibrous nonwoven gatherable web, directly upon a surface of the nonwoven elastic web while the nonwoven elastic web is maintained at its elongated, stretched and biased length. During formation of the fibrous nonwoven gatherable web the nonwoven elastic web is maintained at a stretched length which is at least about 125 percent, that is, at least about one and one quarter of the relaxed, unbiased length of the nonwoven elastic web. For example, the stretched, biased length of the nonwoven elastic web may be maintained in the range of from at least about 125 percent of the relaxed, unbiased length of the nonwoven elastic web to about 700 or more percent of the relaxed, unbiased length of the nonwoven elastic web. The fibrous nonwoven gatherable web is joined to the nonwoven elastic web while the nonwoven elastic web is maintained at its elongated stretched, biased length. This results in the formation of a composite nonwoven elastic web which includes the nonwoven elastic web which is joined to the fibrous nonwoven gatherable web. Because the fibrous nonwoven gatherable web is formed directly onto the surface of the nonwoven elastic web while the nonwoven elastic web is being maintained at its stretched, biased length, the nonwoven elastic web is, at this stage in the process, elongated, stretched and biased and the fibrous nonwoven gatherable web is in an ungathered but gatherable condition. In one aspect, the joining of the fibrous nonwoven gatherable web to the nonwoven elastic web is achieved by heat-bonding to fuse the two webs to each other. The heat-bonding may be carried out within the temperature range of from about 50 degrees centigrade below the melt temperature of at least one of the materials utilized to form at least one of the two webs to about the melt temperature of at least one of the materials utilized to form at least one of the two webs. At high through-put rates the heat-bonding can be carried out above the melt temperature of one or more of the materials utilized to form the webs. The heat-bonding may also be carried out under appropriate conventional pressurized conditions. If desired, conventional sonic bonding techniques may be substituted for the heat-bonding steps.

The application also discloses another embodiment whereby the joining of the fibrous nonwoven gatherable web to the stretched nonwoven elastic web is achieved solely by the entanglement of the individual fibers of the fibrous nonwoven gatherable web with the nonwoven elastic web during formation of the fibrous gatherable web on the surface of the elastic web. If the nonwoven elastic web is a fibrous nonwoven elastic web formed by, for example, meltblowing, entanglement of the individual fibers of the fibrous nonwoven gatherable web with the fibrous nonwoven elastic web is achieved by entanglement of the individual fibers of the fibrous gatherable web with the individual fibers of the fibrous elastic web. If the nonwoven elastic web is an apertured film, joining of the fibrous nonwoven web with the film is achieved by entanglement of the individual fibers of the fibrous gatherable web within the apertures of the film. The joining of the two webs to each other can also be achieved by forming the nonwoven elastic web out of a tacky elastic material, a process that will be discussed hereinafter. In addition, the joining of the two webs to each other may be further enhanced by applying pressure to the two webs after the gatherable web has been formed on the surface of the elastic web. Further improvement in the joining of the two webs can be obtained by applying an adhesive material to the upper surface of the nonwoven elastic web prior to formation of the fibrous nonwoven gatherable web thereon.

After joining of the two webs to each other has been achieved to form a composite elastic web, the biasing force is removed from the composite nonwoven elastic web and the composite elastic web is allowed to relax to its normal relaxed, unbiased length. Because the fibrous nonwoven gatherable web is joined to the nonwoven elastic web while the nonwoven elastic web is stretched, relaxation of the composite nonwoven elastic web results in the gatherable web being carried with the contracting nonwoven elastic web and thus being gathered. After gathering of the fibrous nonwoven gatherable web has occurred by reducing the biasing force on the composite nonwoven elastic web, the composite nonwoven elastic web may be rolled up in rolls for storage and shipment of directed to a manufacturing process for the production of products such as the disposable garments taught by the present application.

As indicated above, the process disclosed in U.S. Pat. No. 4,657,802 can be enhanced by the utilization of a tacky fibrous nonwoven elastic web which can be formed by, for example, meltblowing microfibers of a tacky elastic material such as, for example, an A-B-A' block copolymer or blends of such A-B-A' block copolymers with poly(alpha-methylstyrene) where "A" and "A'" are each thermoplastic polystyrene or polystyrene homolog endblocks and "B" is an elastic polyisoprene midblock. In some embodiments "A" may be the same thermoplastic polystyrene or polystyrene homolog endblock as "A'". The tacky fibrous nonwoven elastic web is then elongated by being stretched to an elongated, stretched length and a fibrous nonwoven gatherable web is formed, for example, by meltblowing or spinbonding the fibrous nonwoven gatherable web, directly upon a surface of the tacky fibrous nonwoven elastic web while maintaining the fibrous nonwoven elastic web at its stretched length. As a result of the fact that the fibrous nonwoven elastic web is tacky, the fibrous nonwoven gatherable web is simultaneously formed upon and adhesively joined to the surface of the tacky fibrous nonwoven elastic web. This results in the formation of a composite nonwoven elastic web having an ungathered fibrous gatherable web adhesively joined to the tacky fibrous nonwoven elastic web with the joining of the two webs to each other being achieved by the adhesive joining which occurs during formation of the fibrous nonwoven gatherable web on the surface of the fibrous nonwoven elastic web. The adhesive joining of the two webs to each other may be increased upon application of pressure to the composite nonwoven elastic web by passing the composite nonwoven elastic web through the nip between rollers, which may be unheated, after the composite web has been formed but before the fibrous tacky nonwoven elastic web is allowed to relax. The adhesive joining may be further enhanced by application of an adhesive material to the surface of the tacky fibrous nonwoven elastic web prior to formation of the gatherable web thereon. The composite nonwoven elastic web is then allowed to relax to its normal relaxed, unbiased length. Because the fibrous nonwoven gatherable web is joined to the tacky fibrous nonwoven elastic web while the tacky fibrous nonwoven elastic web is in a stretched condition, relaxation of the composite nonwoven elastic web and thus the tacky fibrous nonwoven elastic web results in the gatherable web being carried with the contracting fibrous nonwoven elastic web and thus being gathered. After gathering of the fibrous nonwoven gatherable web has occurred the composite nonwoven elastic web may be rolled up in rolls for storage or directly applied to a manufacturing process for the production of disposable garments such as the disposable garments taught by the present application.

The U.S. Pat. No. 4,657,802 is also directed to a composite nonwoven elastic web composed of a nonwoven elastic web that is joined to a gatherable fibrous nonwoven web which has been gathered and with the composite web having been formed by any of the embodiments of the process disclosed above. In particular, the composite nonwoven elastic web, in its relaxed, nonstretched state, is composed of a nonwoven elastic web that is joined to a fibrous nonwoven gathered web which has been gathered as a result of the nonwoven elastic web having been relaxed from an elongated stretched, biased length to a relaxed, unbiased nonstretched length. Exemplary elastomeric materials for use in formation of the fibrous nonwoven elastic web include polyester elastomeric materials, polyurethane elastomeric materials, and polyamide elastomeric materials. Other elastomeric materials for use in formation of the fibrous nonwoven elastic web include (a) A-B-A' block copolymers, where "A" and "A'" are each a thermoplastic polymer endblock which includes a styrenic moiety and where "A" may be the same thermoplastic polymer endblock as "A'", such as a poly(vinyl arene), and where "B" is an elastomeric polymer midblock such as a conjugated diene or a lower alkene or (b) blends of one or more polyolefins or poly(alphamethyl styrene) with A-B-A' block copolymers, where "A" and "A'" are each a thermoplastic polymer endblock which includes a styrenic moiety, where "A" may be the same thermoplastic polymer endblock as "A'", such as a poly(vinyl arene) and where "B" is an elastomeric polymer midblock such as a conjugated diene or a lower alkene. The "A" and "A'" endblocks may be selected from the group including polystyrene and polystyrene homologs and the "B" midblock may be selected from the group including polyisoprene, polybutadiene or poly(ethylene-butylene). If "A" and "A'" are selected from the group including polystyrene or polystyrene homologs and "B" is poly(ethylenebutylene), materials which may be blended with these block copolymers are polymers, including copolymers of ethylene, propylene, butene, other lower alkenes or one or more of these materials. If "A" and "A'" are selected from the group including polystyrene or polystyrene homologs and "B" is a polyisoprene midblock, a material for blending with this type of block copolymer is poly(alpha-methylstyrene).

It is to be clearly understood that the description of methods for making a material suitable for outer cover 20 and the description of materials suitable for use as outer cover 20 is exemplary only and is not meant to be limiting. Other resiliently stretchable materials could be used without departing from the spirit and scope of the present invention.

The bodyside liner 34 may be airlaid, a bonded carded web or a pattern bonded spunbonded web of synthetic fibers such as polypropylene, polyester and the like.

Various materials are contemplated for use as the absorbent core 38, including fibrous materials, foams, particulates, etc. In general, the most economical liquid absorbent material for use in disposable diapers has been an absorbent fiber. The absorbent fiber most commonly used is cellulosic fiber such as comminuted wood pulp, commonly known in the art as "pulp fluff," or simply "fluff."

Comminuted wood pulp (fluff) is preferred as an absorbent fiber, but other cellulose fibers such as cotton linters can be used. The preferred fluff is southern pine kraft wood pulp (i.e., made according to the sulfate process commonly known in the art) which has been bleached, such as can be purchased from International Paper Company.

We claim:

1. An anatomically form-fitting, generally self-adjusting disposable absorbent garment comprising:
   a breathable elastomeric outer cover including front and rear waistband portions defining a waist opening, a pair of leg openings delimited along marginal sides of said outer cover, an intermediate crotch section delimited between said leg openings and front and rear panels separated by said crotch section;
   an absorbent insert structure substantially superposable on said front and rear panels and said crotch section, including a liquid permeable bodyside liner and a liquid impermeable baffle with an absorbent core disposed therebetween;
   attachment means for attaching and integrating said insert to said outer cover while allowing substantially unrestricted functional stretchability thereof; and
   full-length fastening means for releasably securing said garment about a wearer and providing a substantially full-length closure between each of said leg openings and said waist opening, including fixed position primary closure spaced from one another near waist opening and said leg openings, respectively, of said full-length closures, said primary closure being separated by abutment means presenting secondary load-bearing closure means extending substantially between said spaced primary closure means for effecting and maintaining the dimensional integrity of said full-length closure, said full-length fastening means having an effective modulus of elasticity sufficient to allow fastening while also preventing inadvertent disengagement of said fastener members when said garment is worn.

2. The invention of claim 1 wherein said outer cover comprises an elastomeric nonwoven web.

3. The invention of claim 2 wherein said outer cover comprises a stretch-bonded laminar fabric comprising a nonwoven elastic web joined to one or more gatherable nonwoven webs.

4. The invention of claim 1, 2 or 3 further comprising front and rear ear portions delimited along said marginal side edges between said leg openings and said waist opening and wherein said fastening means further comprise front and rear fastener members respectively attached to said front and rear ear portions, each of said front fastener members being releasably engageable with a cooperating one of said rear fastener members to secure said garment about a wearer.

5. The invention of claim 4 wherein said outer cover further comprises a generally hour-glass or T-shaped profile having converging leg openings, defining said front and rear ear portions.

6. The invention of claim 5 wherein said outer cover profile is generally asymmetrical about a central transverse axis of said garment and wherein said rear panel has a large surface area than said front panel.

7. The invention of claim 6 wherein said rear fastener members are respectively attached to the body facing surface of said rear pair of ear portions and said front fastener members are respectively attached to the externally facing surface of said front pair of ear portions, said rear pair of ear portions and said rear pair of fastener members being releasably engageable in overlying relationship with said front pair of ear portions and front pair of fastener members.

8. The invention of claim 4 wherein said primary closure means comprise cooperable snap-in elements.

9. The invention of claim 4 wherein said outer cover is resiliently stretchable from about 20% to about 200%.

10. The invention of claim 9 wherein said outer cover is resiliently stretchable in at least a cross-body direction.

11. The invention of claim 10 wherein said primary closure means have an effective modulus elasticity sufficient to allow fastening while preventing inadvertent disengagement of said fastener members when said garment is being worn, said fastener members cooperating with said resiliently stretchable outer cover to position said insert and secure said garment on the body of a wearer.

12. The invention of claim 11 wherein the effective peel strength of each of said primary closure means is from about 600 grams to about 2500 grams.

13. The invention of claim 12 wherein the effective shear strength of each said secondary closure means is at least about 3750 gram/inch$^2$.

14. The invention of claim 13 wherein the effective diameter of each of said primary closure means is less than about 0.4 inches.

15. The invention of claim 14 wherein the effective thickness of each of said primary closure means is from about 0.01 to about 0.19 inches.

16. The invention of claim 15 wherein $$D/d < 6$$

wherein
   $D$ = the maximum effective diameter of each of said primary closure means and
   $d$ = the minimum effective distance seperating said spaced primary closure means of each of said full-length closures.

17. The invention of claim 16 wherein said secondary closure means comprises cooperable hook and loop materials respectively disposed on cooperating ones of said fastener members.

18. The invention of claim 17 wherein said more abrasive hook portion faces away from the body of a wearer fastened during use.

19. The invention of claim 16 wherein said secondary closure means comprises a cohesive adhesive.

20. The invention of claim 4 wherein said insert is attached and integrated into said outer cover while said outer cover is in a stretched condition.

21. The invention of claim 4 wherein a laterally opposed pair of said front or rear portions have fastener members which are releasably engageable with one another, so that said garment may be neatly and compactly packaged for disposal after use by folding or rolling one of said panels inwardly, bringing said pair of laterally opposed ears together around said rolled or folded panel and fastening said laterally opposed fastener members together.

22. The invention of claim 3 wherein said nonwoven elastic web comprises an A-B-A' block copolymer.

23. The invention of claim 3 wherein either of said elastic nonwoven webs and said one or more gatherable nonwoven webs comprises a polyolefin.

24. The invention of claim 22 wherein either of said elastic nonwoven webs and said one or more gatherable nonwoven webs comprises a polyolefin.

25. The invention of claim 22 wherein said elastic nonwoven web comprises coextrudable polyolefin.

* * * * *